United States Patent
Henderson et al.

(10) Patent No.: US 6,939,709 B2
(45) Date of Patent: Sep. 6, 2005

(54) MULTI-WELL DEVICE

(75) Inventors: Douglas P. Henderson, Basking Ridge, NJ (US); Alan Trieber, Ashland, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/648,662

(22) Filed: Aug. 26, 2003

(65) Prior Publication Data

US 2004/0087005 A1 May 6, 2004

Related U.S. Application Data

(60) Provisional application No. 60/407,031, filed on Aug. 30, 2002.

(51) Int. Cl.[7] ............................................. C12M 1/34
(52) U.S. Cl. ........................ 435/288.4; 435/297.5; 435/305.3; 435/305.4; 422/102
(58) Field of Search .................. 422/102; 435/288.4, 435/297.5, 305.2, 305.3, 305.4

(56) References Cited

U.S. PATENT DOCUMENTS

| | | |
|---|---|---|
| 5,422,270 A | 6/1995 | Caspi |
| 5,652,142 A | 7/1997 | Barker et al. |
| 5,801,055 A | 9/1998 | Henderson |
| 5,972,694 A | 10/1999 | Mathus |
| 6,218,178 B1 | 4/2001 | Banes |

FOREIGN PATENT DOCUMENTS

WO     WO 01/02539 A1     11/2001

*Primary Examiner*—David Redding
(74) *Attorney, Agent, or Firm*—Nanette S. Thomas

(57) ABSTRACT

A multi-well plate assembly has a well plate with a plurality of closed-bottom, open-top wells of substantially uniform square cross-section between the closed bottom and the open top. An insert plate is nested with the well plate and has a top wall substantially covering the open tops of the wells. Inserts project down from the top wall and into the respective wells, such that each insert is nested in a corner of the well. Access ports are formed through the insert plate for alignment with a corner of the respective well opposite the insert. The access port is formed partly through the top wall of the insert plate and partly through the sidewall of the insert.

11 Claims, 7 Drawing Sheets

MULTI-WELL DEVICE

This application claims the benefit of provisional application No. 60/407,031, filed Aug. 30, 2002.

BACKGROUND OF THE INVENTION

1. Field of the Invention

The invention relates to a cell plate assembly for growing cells or tissue cultures in vitro and includes inserts for supporting cells or tissue cultures in a fluid medium that contains nutrients to promote the cell or tissue culture growth.

2. Description of the Related Art

Multi-well plate assemblies have been developed for growing cells or tissue cultures in vitro. The typical multi-well plate assembly includes a well plate with a plurality of wells for containing a fluid medium that has nutrients to promote the cell or tissue culture growth. The multi-well plate assembly further includes an insert plate configured to nest with the well plate. The insert plate includes inserts, each of which has an open top and an open bottom. A porous membrane extends across the open bottom of the insert and is formed from a material that permits the diffusion and transport of ions and macro-molecules across the membrane. The insert extends sufficiently into the well to communicate with the nutrient-rich fluid medium in the well. Thus, a cell layer can be attached and grown on the membrane and can receive nutrients through the microporous membrane from the fluid medium in the well.

The wells must be accessed periodically for adding or removing fluid. This access typically is achieved by access ports that extend through the top wall of the insert plate at locations aligned with the respective wells. The access ports are dimensioned to receive pipettes so that the level of the fluid medium in the well can be adjusted or so that portions of old medium can be aspirated off without removing the insert plate and without contacting the cell or tissue culture that is being grown on the membrane of the insert. Examples of multi-well plate assemblies are shown, for example, in U.S. Pat. Nos. 5,652,142, 5,801,055 and 5,972,694.

Multi-well plate assemblies typically are manufactured with certain standard external dimensions and with certain standard numbers of wells to ensure compatibility with laboratory equipment. One industrial standard includes 96 wells arranged in an 8×12 rectangular matrix. The laboratory equipment includes robotic pipette devices for automatically entering the access ports of the insert plate to adjust the level of fluid in the respective wells. The design of the micro-well plate assemblies should facilitate the robotic insertion of the pipettes into the access port. Thus, both the inserts and the access ports should be as large as possible without exceeding the required center-to-center spacings of the wells and without permitting contamination between the cell or tissue cultures being grown in the inserts and the pipettes being inserted into the access ports.

SUMMARY OF THE INVENTION

The invention is a multi-well plate assembly that comprises a well plate and, an insert plate. The well plate includes a substantially rectangular peripheral skirt with opposed substantially parallel sidewalls and opposed substantially parallel end walls extending perpendicularly between the sidewalls. A corner between one of the end walls and at least one of the sidewalls may be truncated to ensure a required directional orientation for the assembly of the insert plate and the well plate, and hence to prevent cross-contamination if the insert plate is removed and replaced. The well plate further includes a plurality of equally spaced longitudinal walls that extend orthogonally between the end walls of the peripheral skirt and parallel to the sidewalls of the peripheral skirt. The well plate further includes a plurality of equally spaced transverse walls that extend orthogonally between the sidewalls of the peripheral skirt and substantially parallel to the end walls of the peripheral skirt. The longitudinal walls and the transverse walls define a rectangular matrix of substantially square wells within the well plate. Each well has a bottom wall that intersects the respective longitudinal walls and transverse walls of the corresponding well. The bottom walls preferably are not perpendicular to the longitudinal walls and transverse walls of the respective well. Rather, the bottom walls are sloped about a diagonal of the respective wells so that each well has one deep corner and one shallow corner. In a preferred embodiment, as described below, the well plate defines an 8×12 rectangular matrix with a total of 96 wells.

The insert plate includes a substantially rectangular top wall and a peripheral skirt depending down from the top wall. The peripheral skirt of the insert plate is defined by a pair of parallel sidewalls and a pair of parallel end walls extending perpendicularly between the sidewalls. The peripheral skirt of the insert plate is dimensioned to telescope loosely over the peripheral skirt of the well plate. A corner flange is formed adjacent to at least one corner defined at one end wall of the peripheral skirt of the insert plate. The corner flange is dimensioned to nest with the truncated corner of the well plate to ensure only one possible directional orientation of the insert plate on the well plate.

The insert plate further includes a rectangular matrix of inserts at locations that will align with the respective wells when the insert plate is nested over the well plate. Each insert includes a sidewall with an open top at the top wall of the insert plate and a bottom spaced from the top wall of the insert plate by a distance less than the minimum depth of the corresponding well. Thus, each insert will be spaced a selected distance above the bottom wall of the respective well when the insert plate is nested properly over the well plate. A sheet of a porous material is secured over the bottom of each insert. The porous material may be any of the porous materials used on known cell culture inserts and familiar to those skilled in this art.

The sidewall of each insert may be generally frustoconically tapered so that the open top is cross-sectionally larger than the bottom of each insert. Additionally, each insert may be disposed to be approximately tangent to one longitudinal wall and one transverse wall of the respective cell. Accordingly, the cross-sectionally large top of the sidewall of the insert is effectively nested in the corner of the corresponding square cell. However the bottom portions of each frustoconical sidewall are spaced from the wall of the cell to prevent wicking of fluid medium. Preferably, each insert is closest to the shallow corner of the corresponding cell. The sidewall of each insert is not perfectly frustoconical. In particular, each insert includes a notch in the sidewall at a location diagonally opposite the corner of the respective cell in which the insert will nest. Additionally, the sidewall preferably includes an inwardly convex/outwardly concave region extending from the notch toward the bottom end of the respective insert. The convex/concave region preferably is of gradually reduced height at locations closer to the bottom of the respective insert, and preferably effectively defines a zero height at the bottom end of the respective insert, so that the bottom of the respective insert may be substantially circular. For molding efficiency, the internally convex/externally concave region may slope slightly in the same direction as the sidewall, and the radial dimension between the axis of the respective insert and the inwardly convex region of the insert may increase at distances further from the bottom of the respective insert.

The insert plate further includes an access port for each of the inserts. The access ports communicate with the notches in the sidewalls of the respective inserts and preferably are aligned substantially tangent to the corner of the respective well opposite the corner in which the respective insert is nested. Each access port preferably defines an inwardly and downwardly sloped chamfer at the top wall of the insert plate. The chamfer and the notch in the sidewall of the adjacent insert facilitate entry of pipettes into the respective access ports and maximize the effective cross-sectional dimension of each access port without risk of adversely affecting the culture being grown near the bottom of the respective insert. This disposition of each access port aligns the access ports with the deep corners of the respective wells.

The multi-well plate assembly may further comprise a cover. The cover includes a generally planar top wall dimensioned for covering all of the inserts and access ports in the top wall of the insert plate. The cover further includes a downwardly depending skirt dimensioned for telescoping over the skirt of the insert plate.

DETAILED DESCRIPTION

Figure 1:
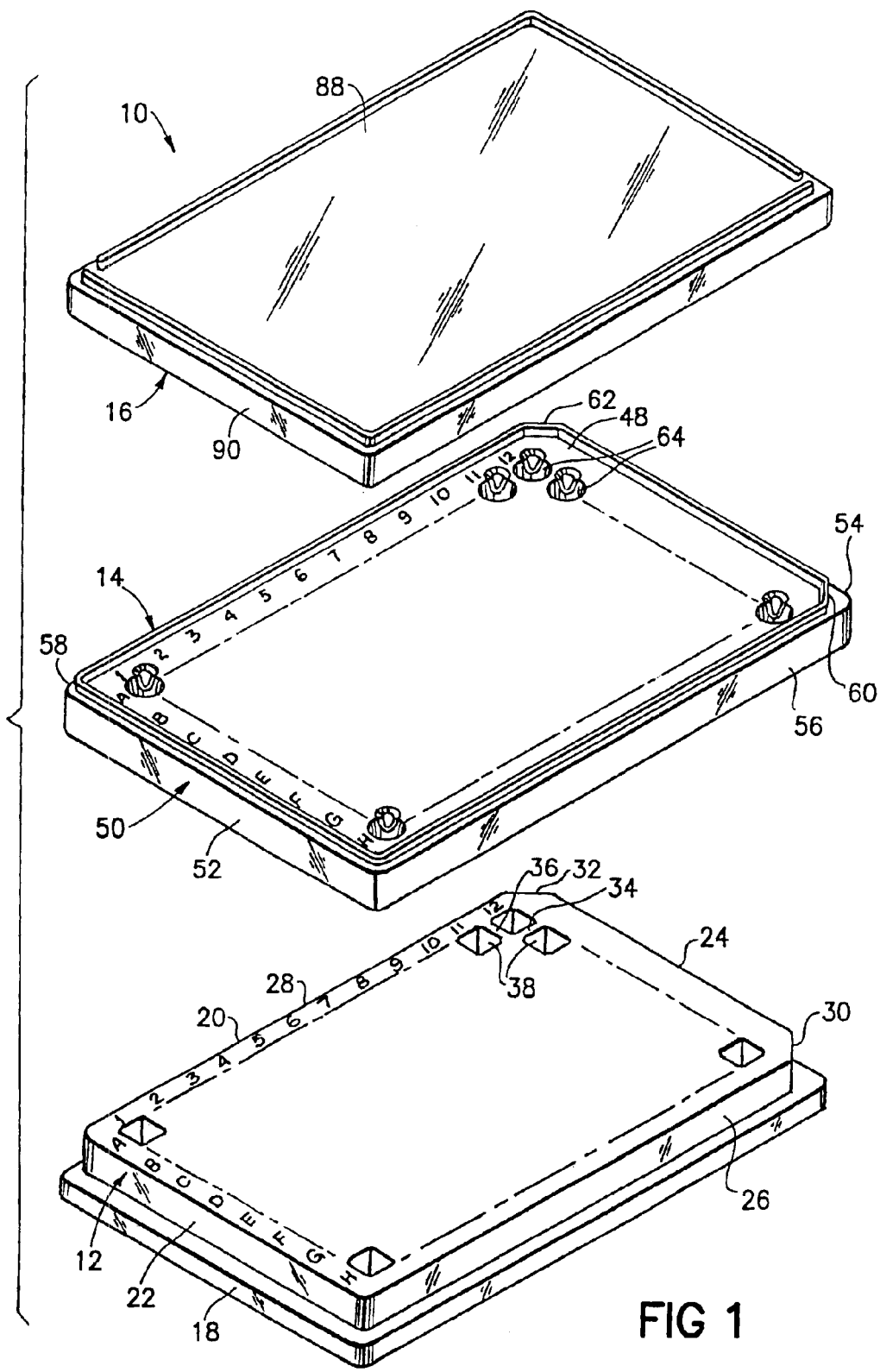
FIG. 1 is an exploded perspective view of a multi-well plate assembly in accordance with the subject invention.
Figure 2:
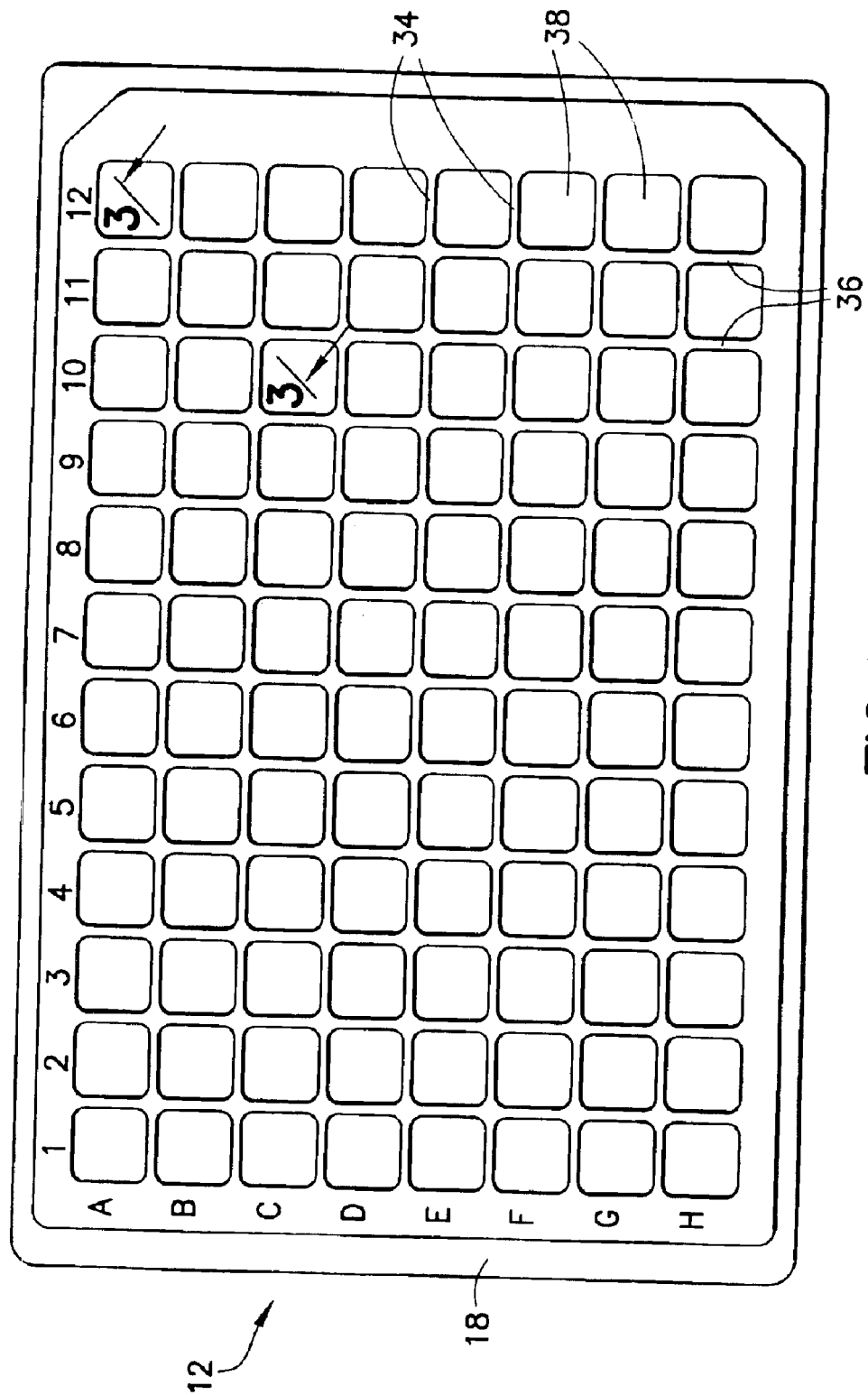
FIG. 2 is a top plan view of the well plate shown in FIG. 1.

A multi-well plate assembly in accordance with the invention is identified generally by the numeral 10 in FIG. 1. Plate assembly 10 includes a well plate 12, an insert plate 14 and a cover 16.

Well plate 12 is molded unitarily from a plastic material such as polyvinylchloride, polystyrene or polypropylene. Well plate 12 has a substantially rectangular base 18 and a peripheral skirt 20 extending upwardly from base 18 and spaced slightly inwardly from the outer periphery of base 18. Peripheral skirt 20 includes first and second substantially parallel end walls 22 and 24 and first and second substantially parallel sidewalls 26 and 28 extending substantially orthogonally between end walls 22 and 24. Truncated corner walls 30 and 32 connect first end wall 22 to first and second sidewalls 26 and 28 respectively. Truncated corner walls 30 and 32 ensure a preferred orientation between well plate 12 and insert plate 14 as explained further herein.

Well plate 12 is further characterized by a plurality of parallel equally spaced longitudinal internal walls 34 aligned parallel to first and second sidewalls 26 and 28. Additionally, well plate 24 includes a plurality of equally spaced parallel transverse internal walls 36 aligned parallel to first and second end walls 22 and 24 and extending between first and second sidewalls 26 and 28. The spacing between longitudinal walls 34 substantially equals the spacing between transverse walls 36. Thus, longitudinal walls 34 and transverse walls 36 define a rectangular array of square cells 38. The dimensions of well plate 12 preferably conform to industrial standards to ensure compatibility with available laboratory equipment. In the illustrated embodiment, well plate 12 includes an 8×12 rectangular array of wells 38, with each well 38 being square and substantially identical to each other well.

Figure 3:
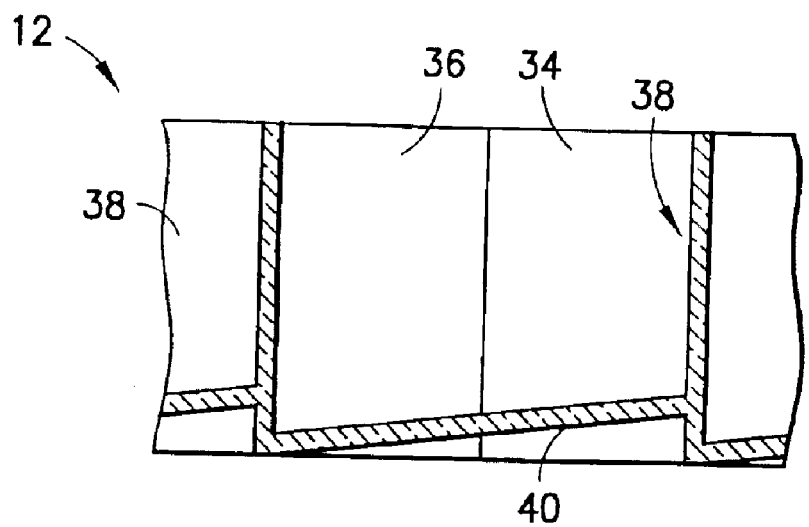
FIG. 3 is a cross-sectional view taken along line 3—3 in FIG. 2.
Figure 5:
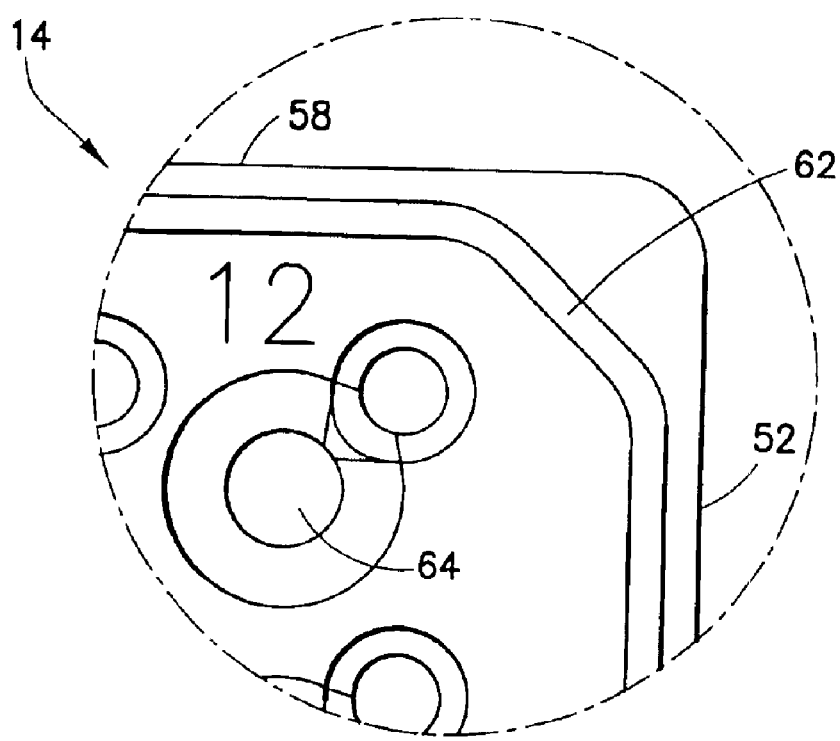
FIG. 5 is an enlarged top view of a portion of the insert plate shown in FIG. 4, and showing one insert and one access port.
Figure 4:
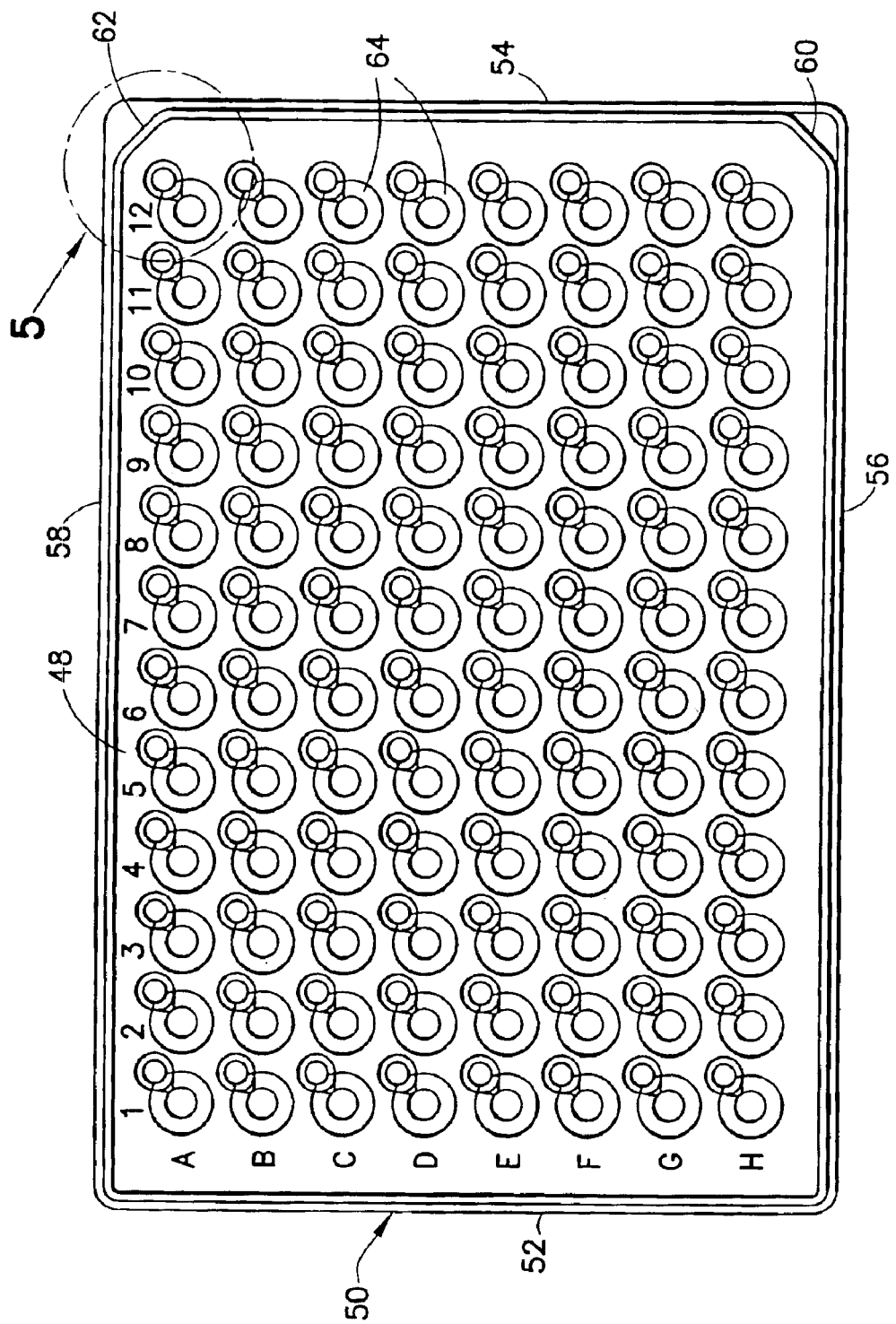
FIG. 4 is a top plan view of an insert plate in accordance with the subject invention.

Each well 38 has an open top, and a closed bottom defined by a bottom wall 40 as shown most clearly in FIG. 3. Bottom wall 40 is aligned at an acute angle to both longitudinal walls 34 and transverse walls 36 of the respective well 38. The angular alignment of bottom wall 40 in each well 38 is such that each well 38 is shallowest at the corner nearest the second end wall 24 and second sidewall 28. Additionally, each well 38 is deepest at the corner closest to first end wall 22 and first sidewall 26.

Insert plate 14 is molded unitarily from a plastic material, such as polyvinylchloride, polystyrene or polypropylene. Insert plate 14 includes a top wall 48 and a peripheral skirt 50. Peripheral skirt 50 of insert plate 14 includes first and second substantially parallel end walls 52 and 54 and first and second substantially parallel sidewalls 56 and 58 that extend substantially orthogonally between end walls 52 and 54. Peripheral skirt 50 of insert plate 14 is dimensioned to telescope loosely over peripheral skirt 20 of well plate 12. Additionally, peripheral skirt 50 is characterized by corner flanges 60 and 62 that nest with chamfered corners 30 and 32 of well plate 12 to ensure a preferred rotational orientation of insert plate 14 on well plate 12. Peripheral skirt 50 extends slightly above top wall 48 to define a peripheral lip extending around top wall 48.

Figure 6:
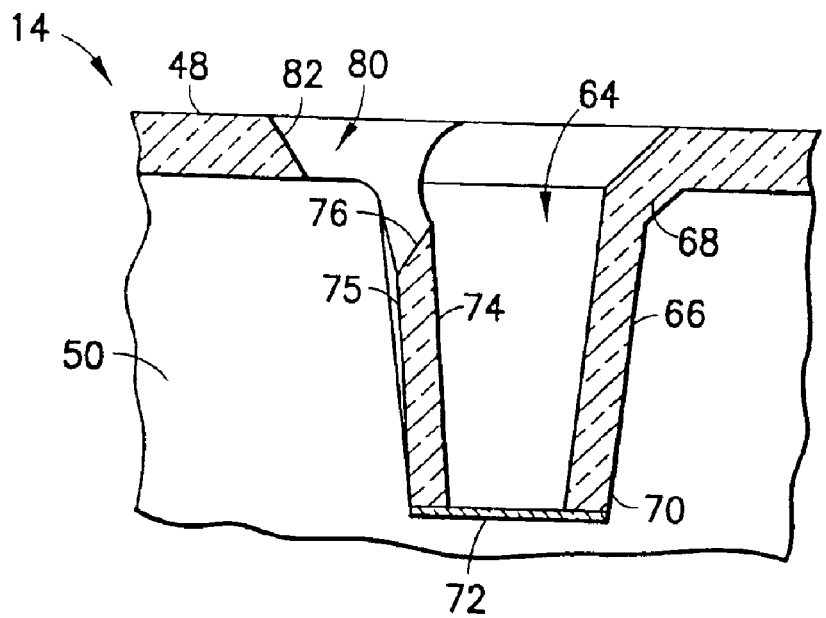
FIG. 6 is a cross-sectional view taken along line 6—6 in FIG. 5.
Figure 7:
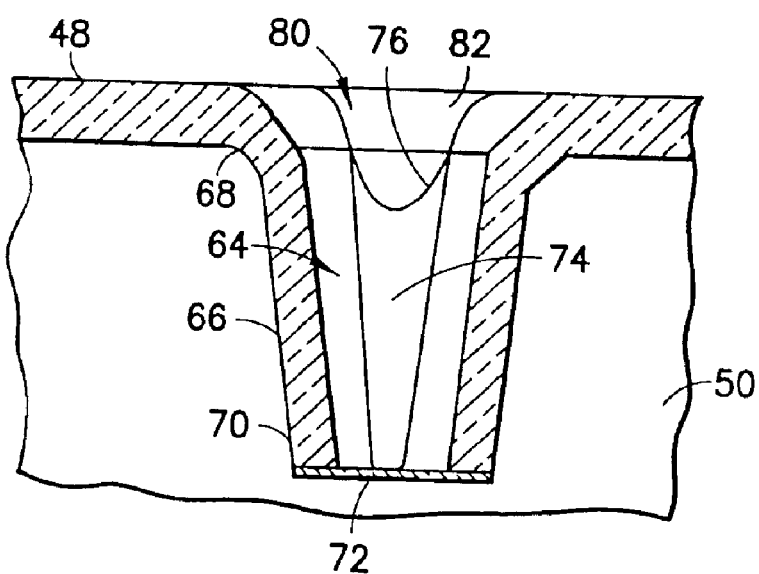
FIG. 7 is a cross-sectional view taken along line 7—7 in FIG. 6.

Insert plate 14 further includes a plurality of inserts 64 that project down from top wall 48. Each insert 64 includes a sidewall 66 with an open top 68 and an open bottom 70, as shown in FIGS. 6 and 7. Top 68 and bottom 70 of each sidewall 66 are generally circularly generated. However top 68 is cross-sectionally larger than bottom 70. Thus, sidewall 66 is generally frustum-shaped. Each insert 64 further includes a semi-permeable, microporous membrane 72 extending entirely across the bottom 70 of sidewall 66.

Inserts 64 are equal in number to wells 38 and are disposed to nest respectively with wells 38. Each insert 64 is disposed in the corner of the corresponding well 38 closest to second sidewall 28 and second end wall 24. Thus, each insert 64 substantially aligns with the shallow corner of the respective well 38. Additionally, each insert 64 is disposed such that the extreme upper portions of sidewall 66 are substantially tangent to the longitudinal wall 34 and the transverse wall 36 that define the shallow corner of well 38.

Sidewall 66 of inserts 64 is are not perfectly frustoconical. Rather, each sidewall 66 includes an elongate region with an inwardly convex surface 74 and an outwardly concave surface 75. Additionally, each sidewall 66 includes a notch 76 extending down from top wall 48 at a location symmetrically registered with inwardly convex/outwardly concave surfaces 74, 75. Surfaces 74 and 75 and notch 76 are disposed on the side of insert 64 that will be diametrically opposite the deep corner of well 38 when insert plate 14 is nested with well plate 12. Each insert 64 defines a length from top wall 48 to membrane 72 that is less than the shallow depth of each well 38. Thus, membrane 72 will be spaced above bottom wall 40 of the corresponding well 38 when insert plate 14 is nested with well plate 12.

Figure 8:
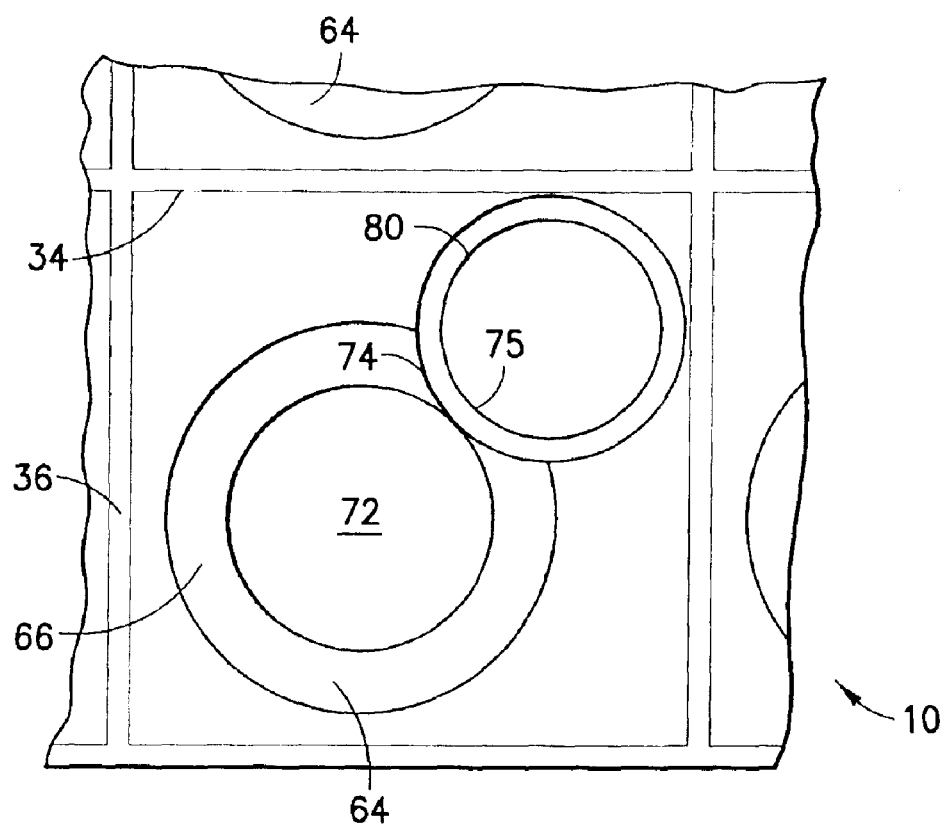
FIG. 8 is a top plan view of a portion of the insert plate and well plate in their assembled condition.
Figure 9:
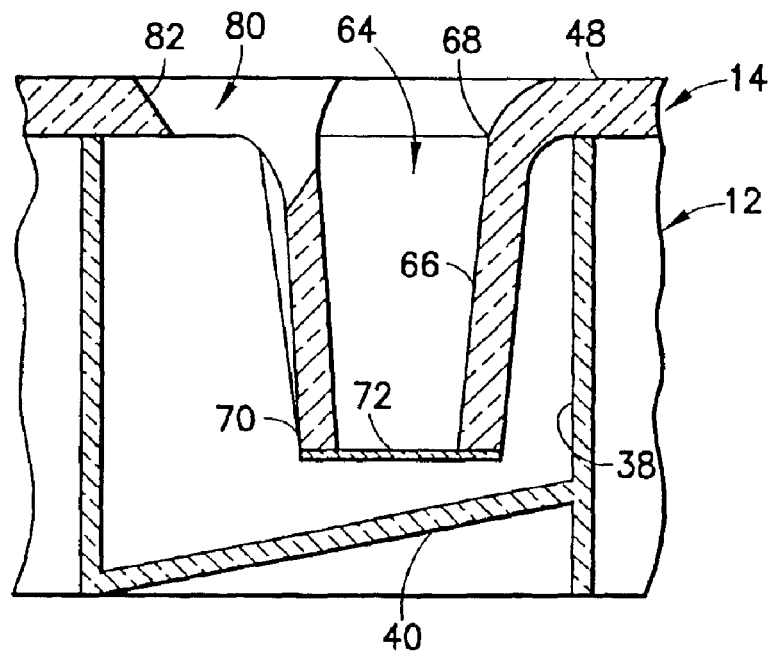
FIG. 9 is a cross-sectional view taken along line 9—9 in FIG. 8.

Top wall 48 of insert plate 14 further is characterized by access ports 80 that communicate respectively with portions of each insert 64 adjacent top end 68 of sidewall 66. Each access port 80 has a circularly generated edge 82 that is chamfered upwardly and inwardly. Additionally, the circle generated by each access port 80 intersects the circularly generated open top 68 of sidewall 66 of insert 64 at a location symmetrically aligned with notch 76. Thus, when viewed from above, each notch 76 defines a continuous extension of the associated access port 80. Furthermore, concave outer surface 75 of each sidewall 66 defines an extension of circular access port 80 when viewed from above. Circular access port 80 is dimensioned and disposed to be substantially tangential to the planes defined by longitudinal walls 34 and transverse walls 36 at the deep end of each well 38. However, a vertical projection of each access port 80 is spaced slightly from circular bottom end 70 of each insert 64. As shown most clearly in FIG. 8, the axis of each insert 64 and the center of the associated access port 80 are aligned along a diagonal plane that will extend from the deep corner to the shallow corner of the respective well 38 when insert plate 14 is nested with well plate 12. The alignment of access port 80 with the deep end of well 38 enables the fluid medium to be aspirated off without tilting assembly 10.

Cover 16 is unitarily molded from a transparent plastic material, such as polyvinylchloride, polystyrene or polypropylene. More particularly, cover 16 includes a substantially rectangular top wall 88 and a downwardly depending rectangular skirt 90. Skirt 90 of cover 16 is dimensioned to telescope loosely over peripheral skirt 50 of insert plate 14.

Multi-well plate assembly 10 is employed by depositing a biological material, such as cells or tissue cultures on membranes 72 of inserts 64 in insert plate 14. Insert plate 14 then is nested with well plate 12. This nesting causes peripheral skirt 50 of insert plate 14 to telescope over peripheral skirt 20 of well plate 12. Additionally, each insert 64 will telescope into a corresponding well 38. Top portions 66 of sidewalls 66 of each insert 64 will be nested in a corner of the corresponding square well 38 closest to second sidewall 28 and second end wall 24 of well plate 14 and will be substantially tangent to the respective longitudinal walls 34 and transverse walls 36 at the shallow corner of well plate 38. The dimensions of sidewall 70 ensure that membrane 72 will be spaced from bottom wall 40 of well 38. However, the fluid deposited into each well 30 will extend to a depth that ensures communication between the fluid and membrane 72. Access ports 80 corresponding to each insert 64 will align with the corresponding well 38 and will be substantially tangent to the longitudinal wall 34 and transverse wall 36 defining the deeper corner of the respective well 38. This orientation of insert 64 and access port 80 along a diagonal plane of well 38 enables efficiently large cross-sections for both insert 64 and access port 80 relative to the available space allotted for each well 38. Thus, pipettes are inserted easily into access ports 80 for periodically replenishing fluid growth material in wells 38 or for removing excess fluid therefrom. More particularly, a pipette can be inserted into access port 80, while employing portions of notch 76 extending into a space that would otherwise be part of insert 64. However, access port 80 and notch 76 both are offset horizontally from membrane 72, and hence a downwardly moving pipette will not interfere with or contaminate a culture being grown on membrane 72. Accordingly, a large and conveniently accessible access port 80 is provided within a very small space.

Figure 10:
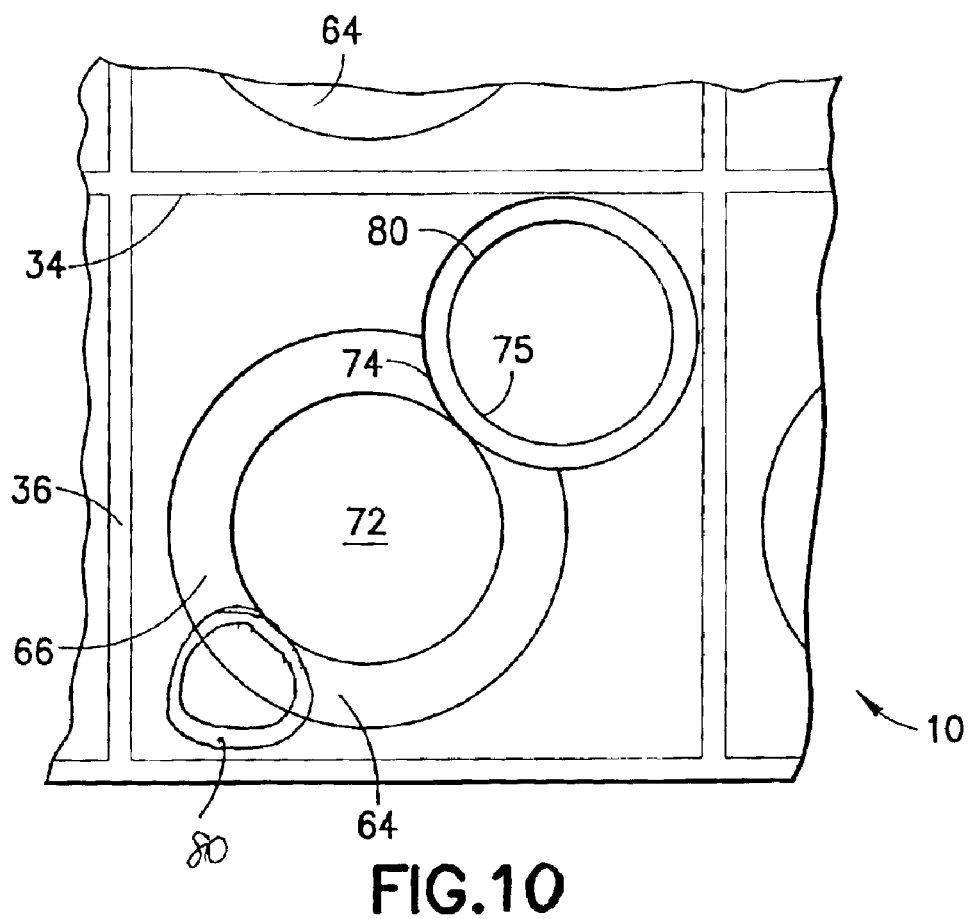
FIG. 10 is a top plan view of a portion of an alternative insert plate and well plate in their assembled condition.

Although not shown in the figures, it is within the purview of this invention that the insert plate 14 and each insert 64 may include a plurality of access ports 80 that communicate respectively with portions of each insert 64. It is also within the purview of this invention that the geometry of the plurality of access ports associated with each insert may be the same or of different geometry. An example of the plurality of access ports 80 is shown in FIG. 10.

What is claimed is:

1. A multi-well plate assembly having a well plate with a plurality of upwardly open wells, each said well having a substantially square cross-section with pairs of adjacent walls defining pairs of opposed corners in each said well, an insert plate nested with said well plate, said insert plate having a top wall for substantially covering all of said wells of said well plate, said top wall being formed with a plurality of inserts aligned respectively with said wells, each said insert having a sidewall projecting down from said top wall and being substantially nested in one said corner of said well, a plurality of access ports aligned respectively with said wells, each said access port being substantially adjacent a corner of said well opposite said corner in which said insert sidewall is nested, said access port including a first portion formed through said top wall and a second portion defining a notch formed in said sidewall of said insert adjacent said top wall of said insert plate.

2. The multi-well plate assembly of claim , further comprising a cover nested over said insert plate.

3. The multi-well plate assembly of claim 1, wherein each said well has a bottom wall, and wherein said sidewall of each said insert is spaced from said bottom wall of said respective well.

4. The multi-well plate assembly of claim 3, wherein each said insert further comprises a porous membrane secured to said bottom of said sidewall.

5. The multi-well plate assembly of claim 4, wherein each said insert includes an inwardly convex and an outwardly concave portion aligned with said notch of said access port, whereby a pipette can be inserted at least partly into said access port and said outwardly concave portion of said sidewall.

6. The multi-well plate assembly of claim 1, wherein portions of said access port formed on said top wall of said insert plate are chamfered downwardly and inwardly toward said respective well.

7. The multi-well plate assembly of claim 6, wherein portions of said access port defined by said notch are chamfered downwardly and inwardly into said respective well.

8. The multi-well access port of claim 3, wherein said sidewall of each of said inserts is disposed substantially tangent to two of said adjacent walls defining one of said corners of said respective well.

9. The multi-well plate assembly of claim 8, wherein each of said access ports is aligned substantially tangent to two of said adjacent walls defining one of said corners of said well opposite said corner in which said sidewall of said insert is nested.

10. The multi-well plate assembly of claim 3, wherein the bottom wall of each said well is sloped, such that said well has a deep corner and a shallow corner, said insert being nested in said shallow corner of said well.

11. A multi-well plate assembly comprising:
- a plate having a top surface and a plurality of well components;
- said well components each having an upper portion, a lower chamber, and a sidewall extending between said upper portion and said lower chamber;
- said upper portion having an upper chamber and at least two access ports;
- a membrane separating said upper chamber from said lower chamber; and
- said access ports each including a first portion formed through said top surface and a second portion defining a step formed with said sidewall.

* * * * *